United States Patent
Herold et al.

(10) Patent No.: US 8,058,307 B2
(45) Date of Patent: Nov. 15, 2011

(54) ALCANOIC ACID AMIDES SUBSTITUTED BY SATURATED O-HETEROCYCLES

(75) Inventors: Peter Herold, Allschwil (CH); Robert Mah, Allschwil (CH); Vincenzo Tschinke, Allschwil (CH); Stefan Stutz, Allschwil (CH); Aleksandar Stojanovic, Allschwil (CH); Stjepan Jelakovic, Allschwil (CH); Christiane Marti, Allschwil (CH)

(73) Assignee: Novartis AG, Basel (CH)

( * ) Notice: Subject to any disclaimer, the term of this patent is extended or adjusted under 35 U.S.C. 154(b) by 675 days.

(21) Appl. No.: 11/992,127

(22) PCT Filed: Sep. 14, 2006

(86) PCT No.: PCT/EP2006/066368
§ 371 (c)(1),
(2), (4) Date: Mar. 17, 2008

(87) PCT Pub. No.: WO2007/031557
PCT Pub. Date: Mar. 22, 2007

(65) Prior Publication Data
US 2009/0275651 A1  Nov. 5, 2009

(30) Foreign Application Priority Data
Sep. 17, 2005  (CH) ..................... 1518/05

(51) Int. Cl.
*A61K 31/38* (2006.01)
*A61K 31/355* (2006.01)
*A61K 31/35* (2006.01)
*C07D 335/06* (2006.01)
*C07D 311/00* (2006.01)
*C07D 315/00* (2006.01)
*C07D 215/00* (2006.01)

(52) U.S. Cl. ........ 514/432; 514/458; 514/459; 546/152; 549/23; 549/396; 549/426

(58) Field of Classification Search ............... 514/459, 514/471, 432, 458; 549/426, 496, 23, 396; 546/152
See application file for complete search history.

(56) References Cited

U.S. PATENT DOCUMENTS
5,627,182 A  5/1997  Göschke et al.

FOREIGN PATENT DOCUMENTS
WO  2006/061427  6/2006
WO  2006/095020  9/2006

OTHER PUBLICATIONS

International Search Report issued Apr. 3, 2007 in the International (PCT) Application PCT/EP2006/066368 of which the present application is the U.S. National Stage.
Written Opinion in the International (PCT) Application PCT/EP2006/066368 of which the present application is the U.S. National Stage, Mar. 4, 2007.
Jeanette M. Wood et al., "Structure-based design of aliskiren, a novel orally effective renin inhibitor", Biochemical and Biophysical Research Communications, Academic Press Inc., vol. 308, No. 4, pp. 698-705, XP004447169, ISSN: 0006-291X, Sep. 5, 2003.
Richard Göschke et al., "Design and Synthesis of Novel 2,7-Dialkyl Substituted 5(S)-Amino-4(S)-Hydroxy-8-Phenyl-Octanecarboxamides as In Vitro Potent Peptidomimetic Inhibitors of Human Renin", Bioorganic & Medicinal Chemistry Letters, vol. 7, No. 21, pp. 2735-2740, XP004136522, ISSN: 0960-894X, Nov. 4, 1997.

*Primary Examiner* — Victor Oh
(74) *Attorney, Agent, or Firm* — Wenderoth, Lind & Ponack, L.L.P.

(57) ABSTRACT

Compounds of the general formula (formula I) in which the meanings of the substituents R1 to R6 are as indicated in claim 1, have renin-inhibiting properties and can be used as medicines.

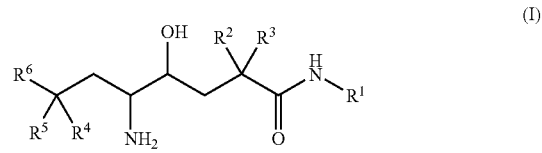

10 Claims, No Drawings

ALCANOIC ACID AMIDES SUBSTITUTED BY SATURATED O-HETEROCYCLES

The present invention relates to the use of specific alkanamides as medicines, in particular as renin inhibitors, to a process for their preparation and to novel compounds of this type.

Alkanamides for use as medicines are disclosed for example in EP 678503. In relation especially to the renin inhibition, however, there is still a need for active ingredients of high potency. The priority in this is to improve the pharmacokinetic properties. These properties, which aim at better bioavailability, are for example absorption, metabolic stability, solubility or lipophilicity.

The invention therefore provides compounds and the use of compounds of the general formula

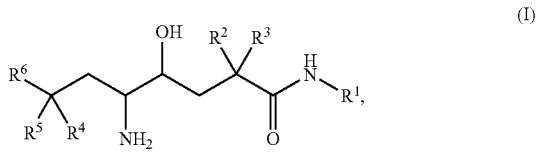

(I)

in which
$R^1$ is saturated heterocyclyl or saturated heterocyclyl-$C_{1-4}$alkyl, where in each case the heterocycle is an oxygen-heterocycle having 1 or 2 oxygen atoms, is bonded via a C atom and is unsubstituted or substituted one or more times by $C_{1-6}$alkanoyl, $C_{2-6}$alkenyl, $C_{2-6}$alkynyl, $C_{1-6}$alkoxy, $C_{1-6}$alkoxy-$C_{1-6}$alkoxy, $C_{1-6}$alkoxy-$C_{1-6}$alkyl, $C_{1-6}$alkoxycarbonylamino, $C_{1-6}$alkyl, $C_{1-6}$alkylcarbonylamino, $C_{1-6}$alkylcarbonyloxy, $C_{1-6}$alkylenedioxy, optionally N-mono- or N,N-di-$C_{1-6}$alkylated amino, aryl, optionally N-mono- or N,N-di-$C_{1-6}$alkylated carbamoyl, optionally esterified carboxy, cyano, $C_{3-8}$cycloalkoxy, $C_{3-8}$cycloalkyl-$C_{0-6}$alkyl, halogen, halo-$C_{1-6}$alkoxy, halo-$C_{1-6}$alkyl, heteroaryl, unsaturated, partially saturated or saturated heterocyclyl, hydroxy, nitro or oxo;
$R^2$ and $R^3$ are independently of one another hydrogen, $C_{1-6}$alkyl, $C_{2-6}$alkenyl or $C_{2-6}$alkynyl, or the two radicals together with the carbon atom to which they are bonded are $C_{3-8}$cycloalkyl;
$R^4$ and $R^5$ are independently of one another hydrogen, $C_{1-6}$alkyl, $C_{2-6}$alkenyl or $C_{2-6}$alkynyl or the two radicals together with the carbon atom to which they are bonded are $C_{3-8}$cycloalkyl;
$R^6$ is a group —$CH_2$—$R^7$, —$CH_2$—CO—$R^7$, —$CH_2$—$CH_2$—$R^7$, —$CH_2$—$NR^8$—CO—$R^7$, —$CH_2$—CO—$NR^8$—$CH_2$—$R^7$, —$CH_2$—$CH_2$—$NR^8$—$R^7$, —$CH_2$—CO—$NR^8$—$R^7$ or —CO—$NR^8$—$CH_2$—$R^7$;
$R^7$ is an optionally substituted cyclic radical;
$R^8$ is hydrogen, $C_{1-6}$alkyl or $C_{1-6}$alkanoyl;
and salts, especially pharmaceutically useful salts thereof.

The term saturated oxygen-heterocycle refers to 3-16-membered, mono- or bicyclic saturated heterocyclic radicals having 1 or 2 oxygen atoms. Preferred radicals have 3-8 members, particularly preferably 5 or 6 members, and are monocyclic and are optionally fused to a 3-8-membered ring which may be carbocyclic or heterocyclic. A further preferred group of saturated oxygen-heterocyclic radicals are bicyclic saturated oxygen-heterocycles which have a spirocyclic or bridged ring. Preferred oxygen-heterocyclic radicals have in each ring 1 oxygen atom or 1-2 oxygen atoms, with at least two, preferably 2-7, carbon atoms being present in each ring. Examples of saturated oxygen-heterocyclyl radicals are dioxanyl, [1,4]dioxepanyl, dioxolanyl, oxepanyl, tetrahydropyranyl and tetrahydrofuranyl. Examples of bicyclic saturated oxygen-heterocyclyl radicals are 2,5-dioxabicyclo[4.1.0]heptanyl, 2-oxabicyclo[2.2.1]heptanyl, 2-oxabicyclo[4.1.0]heptanyl, 3-oxabicyclo[4.1.0]heptanyl, 7-oxabicyclo[2.2.1]heptanyl, 2-oxabicyclo[3.1.0]hexanyl, 3-oxabicyclo[3.1.0]hexanyl, 1-oxaspiro[2.5]octanyl, 6-oxaspiro[2.5]octanyl or 3-oxabicyclo[3.3.1]nonanyl. Oxygen-heterocyclyl may be unsubstituted or substituted one or more times, e.g. once or twice, by $C_{1-6}$alkanoyl, $C_{2-6}$alkenyl, $C_{2-6}$alkynyl, $C_{1-6}$alkoxy, $C_{1-6}$alkoxy-$C_{1-6}$alkoxy, $C_{1-6}$alkoxy-$C_{1-6}$alkyl, $C_{1-6}$alkoxycarbonylamino, $C_{1-6}$alkyl, $C_{0-6}$alkylcarbonylamino, $C_{1-6}$alkylcarbonyloxy, $C_{1-6}$alkylenedioxy, optionally N-mono- or N,N-di-$C_{1-6}$alkylated amino, aryl, optionally N-mono- or N,N-di-$C_{1-6}$alkylated carbamoyl, optionally esterified carboxy, cyano, $C_{3-8}$cycloalkoxy, $C_{3-8}$cycloalkyl-$C_{0-6}$alkyl, halogen, halo-$C_{1-6}$alkoxy, halo-$C_{1-6}$alkyl, heteroaryl, unsaturated, partially saturated or saturated heterocyclyl, hydroxy, nitro, oxide or oxo.

The term saturated heterocyclyl refers to 3-16-membered, mono- or bicyclic saturated heterocyclic radicals having 1 to 4 nitrogen and/or 1 or 2 sulphur or oxygen atoms. Preferred radicals have 3-8 members, particularly preferably 5 or 6 members, and are monocyclic and are optionally fused to a 3-8-membered ring which may be carbocyclic or heterocyclic. A further preferred group of saturated heterocyclic radicals are bicyclic saturated heterocycles which have a spirocyclic or bridged ring. Preferred heterocyclic radicals have in each ring 1 nitrogen, oxygen or sulphur atom or 1-2 nitrogen atoms and 1-2 oxygen atoms 1-2 nitrogen atoms and 1-2 sulphur atoms, with at least one, preferably 1-7, carbon atom(s) being present in each ring. Examples of saturated heterocyclyl radicals are azepanyl, azetidinyl, aziridinyl, dioxanyl, [1,4]dioxepanyl, dioxolanyl, dithianyl, dithiolanyl, morpholinyl, oxathianyl, oxepanyl, piperazinyl, piperidinyl, pyrrolidinyl, tetrahydropyranyl, tetrahydrofuranyl, tetrahydrothiophenyl, tetrahydrothiopyranyl, thiepanyl or thiomorpholinyl. Examples of bicyclic saturated heterocyclyl radicals are 2,5-dioxabicyclo[4.1.0]heptanyl, 2-oxabicyclo[2.2.1]heptanyl, 2-oxabicyclo[4.1.0]heptanyl, 3-oxabicyclo[4.1.0]heptanyl, 7-oxabicyclo[2.2.1]heptanyl, 2-oxabicyclo[3.1.0]hexanyl, 3-oxabicyclo[3.1.0]hexanyl, 1-oxaspiro[2.5]octanyl, 6-oxaspiro[2.5]octanyl or 3-oxabicyclo[3.3.1]nonanyl. Heterocyclyl may be unsubstituted or substituted one or more times, e.g. once or twice, by $C_{1-6}$alkanoyl, $C_{2-6}$alkenyl, $C_{2-6}$alkynyl, $C_{1-6}$alkoxy, $C_{1-6}$alkoxy-$C_{1-6}$alkoxy, $C_{1-6}$alkoxy-$C_{1-6}$alkyl, $C_{1-6}$alkoxycarbonylamino, $C_{1-6}$alkyl, $C_{1-6}$alkylcarbonylamino, $C_{1-6}$alkylcarbonyloxy, $C_{1-6}$alkylenedioxy, optionally N-mono- or N,N-di-$C_{1-6}$alkylated amino, aryl, optionally N-mono- or N,N-di-$C_{1-6}$alkylated carbamoyl, optionally esterified carboxy, cyano, $C_{3-8}$cycloalkoxy, $C_{3-8}$cycloalkyl-$C_{0-6}$alkyl, halogen, halo$C_{1-6}$ alkoxy, halo-$C_{1-6}$alkyl, heteroaryl, unsaturated, partially saturated or saturated heterocyclyl, hydroxy, nitro, oxide or oxo.

The term cyclic radical refers to carbocyclic and heterocyclic radicals. These radicals may be saturated, partially saturated, unsaturated or aromatic. Examples of substituents on $R^7$ are acetamidinyl-$C_{1-6}$alkyl, 3-acetamidomethylpyrrolidinyl, acyl-$C_{1-6}$alkoxy-$C_{1-6}$alkyl, (N-acyl)-$C_{1-6}$alkoxy-$C_{1-6}$alkylamino, $C_{1-6}$alkanoyl, $C_{3-5}$alkenyloxy-$C_{1-6}$alkyl, $C_{1-6}$alkoxy, $C_{1-6}$alkoxy-$C_{1-6}$alkoxy, $C_{1-6}$alkoxy-$C_{1-6}$alkoxy-$C_{1-6}$alkyl, $C_{1-6}$alkoxy-$C_{1-6}$alkyl, (N—$C_{1-6}$alkoxy)-$C_{1-6}$alkyl-aminocarbonyl-$C_{1-6}$alkoxy, (N—$C_{1-6}$alkoxy-$C_{1-6}$ alkylaminocarbonyl-$C_{1-4}$alkyl, $C_{1-6}$alkoxy-$C_{1-6}$alkylcarbamoyl, $C_{1-6}$alkoxy-$C_{1-6}$alkylcarbonyl, $C_{1-6}$alkoxy-$C_{1-6}$alkylcarbonylamino, 1-$C_{1-6}$alkoxy-$C_{1-6}$alkylimidazol-2-yl, 2-$C_{1-6}$alkoxy-$C_{1-6}$alkyl-4-oxo-imidazol-1-yl, 3-$C_{1-6}$alkoxy-$C_{1-6}$alkyl-pyrrolidinyl, 1-$C_{1-6}$alkoxy-$C_{1-6}$alkyltetrazol-5-yl, 5-$C_1$-alkoxy-$C_{1-6}$alkyltetrazol-1-yl, $C_{1-6}$alkoxy-aminocarbonyl-$C_{1-6}$alkyl, $C_{1-6}$alkoxyaminocarbonyl-$C_{1-6}$alkyl, $C_{1-6}$alkoxycarbonyl, $C_{1-6}$alkoxy-carbonyl-$C_{1-6}$alkoxy, $C_{1-6}$alkoxycarbonyl-$C_{1-6}$-alkyl, $C_{1-4}$alkoxycarbonylamino, $C_{1-6}$alkoxy-carbonylamino-$C_{1-6}$alkoxy, $C_{1-6}$alkoxycarbonylamino-$C_{1-6}$alkyl, $C_{1-6}$alkyl, (N—$C_{1-6}$alkyl)-$C_{1-6}$alkoxy-$C_{1-6}$ alkylcarbamoyl, (N—$C_{1-6}$alkyl)-$C_{1-6}$alkoxy-$C_{1-6}$-alkylcarbonylamino, (N—$C_{1-6}$alkyl)-$C_{1-6}$-alkoxycarbonylamino, (N—$C_{1-6}$alkyl)-$C_{1-6}$-alkylcarbonylamino-$C_{1-6}$alkoxy, (N—$C_{1-6}$alkyl)-$C_{0-6}$alkylcarbonylamino-$C_{1-6}$alkyl, (N—$C_{1-6}$alkyl)$C_{1-6}$-alkylsulphonylamino-$C_{1-6}$alkoxy, (N—$C_{1-6}$alkyl)-$C_{1-6}$alkylsulphonylamino-$C_{1-6}$alkyl, $C_{1-6}$alkylamidinyl, $C_{1-6}$alkylamino, di-$C_{1-6}$alkylamino, $C_{1-6}$alkylamino-$C_{2-6}$alkoxy, di-$C_{1-6}$alkylamino-$C_{2-6}$alkoxy, $C_{1-6}$alkylamino-$C_{1-6}$alkyl, $C_{1-6}$alkylaminocarbonyl, $C_{1-6}$alkylaminocarbonyl-$C_1$-alkoxy, di-$C_{1-6}$alkylaminocarbonyl-$C_1$-alkoxy, $C_{1-6}$alkylaminocarbonyl-$C_{1-6}$alkoxy-$C_{1-6}$alkyl, $C_{1-6}$alkylaminocarbonyl-$C_{1-6}$alkyl, $C_{1-6}$alkyl-aminocarbonylamino-$C_{1-6}$alkoxy, $C_{1-6}$alkylaminocarbonylamino-$C_{1-6}$alkyl, di-$C_{1-6}$alkyl-aminocarbonyl-$C_{1-6}$alkyl, di-$C_{1-6}$alkylamino-$C_{1-6}$alkyl, $C_{1-6}$alkylcarbamoyl, di-$C_{1-6}$alkylcarbamoyl, $C_{0-6}$alkylcarbonylamino, $C_{0-6}$alkylcarbonylamino-$C_{1-6}$alkoxy, $C_{0-6}$alkylcarbonylamino-$C_1$-alkyl, $C_{1-6}$-alkylcarbonyloxy-$C_{1-6}$alkoxy, $C_{1-6}$alkylcarbonyloxy-$C_{1-6}$alkyl, $C_{1-6}$alkylsulphonyl, $C_{1-6}$alkylsulphonyl-$C_{1-6}$alkoxy, $C_{1-6}$alkylsulphonyl-$C_{1-6}$alkyl, $C_{1-6}$alkylsulphonylamino-$C_{1-6}$alkoxy, $C_{1-6}$alkylsulphonylamino-$C_{1-6}$alkyl, amino-$C_{2-7}$alkoxy, amino-$C_{1-4}$alkyl, carbamoyl, carbamoyl-$C_{1-6}$alkoxy, carbamoyl-$C_{1-6}$alkyl, carboxy-$C_{1-6}$alkoxy, carboxy-$C_{1-6}$alkoxy-$C_{1-6}$alkyl, carboxy-$C_{1-6}$-alkyl, cyano, cyano-$C_{1-6}$alkoxy, cyano-$C_{1-6}$alkyl, $C_{3-8}$cycloalkyl-$C_{0-6}$alkoxy, $C_{3-8}$cycloalkyl-$C_{1-6}$alkyl, $C_{3-8}$cycloalkylcarbonylamino, $C_{3-8}$cycloalkylcarbonylamino-$C_{1-6}$alkoxy, $C_{3-8}$cycloalkylcarbonylamino-$C_{1-6}$alkyl, 3,4-dihydroxypyrrolidinyl, O,N-dimethylhydroxylamino-$C_{1-6}$-alkyl, 2,6-dimethylmorpholinyl, 3,5-dimethylmorpholinyl, dioxanyl, dioxolanyl, 4,4-dioxothiomorpholinyl, dithianyl, dithiolanyl, halogen, halo-$C_{1-7}$alkoxy, halo-$C_{1-6}$alkyl, hydroxy-$C_{1-6}$alkoxy-$C_{1-6}$-alkoxy, hydroxy-$C_{1-6}$-alkoxy-$C_{1-6}$alkyl, hydroxy-$C_{1-6}$alkyl, (N-hydroxy)-$C_{1-6}$alkylaminocarbonyl-$C_{1-6}$alkoxy, (N-hydroxy)$C_{1-6}$alkylaminocarbonyl-$C_{1-6}$alkyl, (N-hydroxy)aminocarbonyl$C_{1-6}$alkoxy, (N-hydroxy)aminocarbonyl-$C_{1-6}$alkyl, 2-hydroxymethylpyrrolidinyl, 4-hydroxypiperidinyl, 3-hydroxypyrrolidinyl, imidazolyl-$C_{1-4}$alkoxy, imidazolyl-$C_{1-4}$alkyl, 2-methylimidazolyl-$C_{1-4}$alkoxy, 2-methylimidazolyl-$C_{1-4}$alkyl, 3-methyl-[1,2,4]-oxadiazol-5-yl-$C_{1-4}$alkoxy, 5-methyl-[1,2,4]-oxadiazol-3-yl-$C_{1-4}$alkoxy, 3-methyl-[1,2,4]-oxadiazol-5-yl-$C_{1-4}$alkyl, 5-methyl-[1,2,4]-oxadiazol-3-yl-$C_{1-4}$alkyl, O-methyloximyl-$C_{1-6}$-alkyl, 4-methylpiperazinyl, 5-methyltetrazol-1-yl-$C_{1-4}$alkoxy, 5-methyltetrazol-1-yl-$C_{1-4}$alkyl, morpholinyl, [1,2,4]-oxadiazol-5-yl-$C_{1-4}$alkoxy, [1,2,4]-oxadiazol-5-yl-$C_{1-4}$alkyl, oxazol-4-yl-$C_{1-4}$alkoxy, oxazol-4-yl-$C_{1-4}$alkyl, oxide, oxo, 2-oxoimidazolidinyl, 2-oxo-[1,3]oxazinyl, 2-oxo-oxazolidinyl, 2-oxooxazolidinyl-$C_{1-4}$alkoxy, 2-oxooxazolidinyl-$C_{1-4}$alkyl, 4-oxopiperidinyl, 2-oxopyrrolidinyl, 2-oxopyrrolidinyl-$C_{1-4}$alkoxy, 2-oxopyrrolidinyl-$C_{1-4}$ alkyl, 2-oxotetrahydro-pyrimidinyl, 4-oxothiomorpholinyl, piperazinyl, piperidinyl, pyrrolidinyl, pyrrolyl, tetrazol-1-yl-$C_{1-4}$alkoxy, tetrazol-2-yl-$C_{1-4}$alkoxy, tetrazol-5-yl-$C_{1-4}$alkoxy, tetrazol-1-yl-$C_{1-4}$alkyl, tetrazol-2-yl-$C_{1-4}$alkyl, tetrazol-5-yl-$C_{1-4}$alkyl, thiazolyl-4-yl-$C_{1-4}$alkoxy, thiazol-4-yl-$C_{1-4}$ alkyl, thiomorpholinyl, [1,2,4]-triazol-1-yl-$C_{1-4}$alkoxy, [1,2,4]-triazol-4-yl-$C_{1-4}$alkoxy, [1,2,4]-triazol-1-yl-$C_{1-4}$ alkyl or [1,2,4]-triazol-4-yl-$C_{1-4}$alkyl.

Carbocyclic saturated radicals are for example $C_{3-8}$cycloalkyl radicals or else bicyclic (including spirocyclic) and polycyclic radicals having up to 20 carbon atoms.

Carbocyclic partially saturated radicals are derived from the saturated radicals mentioned and have at least one double bond.

Carbocyclic aromatic radicals are for example phenyl or naphthyl or else mono-, bi- or polycyclic radicals having up to 20 carbon atoms.

Heterocyclic partially saturated radicals are derived from the saturated or unsaturated radicals mentioned and have at least one double bond. They are for example 2,3-dihydrobenzoimidazol-1-yl, 3,4-dihydro-2H-1,4-benzoxazin-4-yl, 3,4-dihydro-2H-1,4-benzothiazin-4-yl, 3,4-dihydro-2H-1,3-benzothiazin-1-yl, 5,6-dihydrophenanthridin-5-yl, 3,4,5,6,7,8-hexahydro-2H-1,4-benzoxazin-4-yl, 3,4,5,6,7,8-hexahydro-2H-1,4-benzothiazin-4-yl, 2,3,4,5-tetrahydro-1H-1-benzo[6,7-b]azepin-1-yl, 1,2,3,4-tetrahydro-1,3-benzodiazin-1-yl or -3-yl, 1,2,3,4-tetrahydro-1,4-benzodiazin-1-yl, 1,2,3,4-tetrahydroquinol-1-yl or 1,2,3,4-tetrahydroisoquinol-2-yl.

Heterocyclic aromatic radicals are for example benzofuranyl, benzoimidazolyl, benzooxazinyl, benzooxazolyl, benzothiazinyl, benzothiazolyl, benzo[b]thienyl, quinazolinyl, quinolyl, quinoxalinyl, furanyl, imidazolyl, imidazopyridinyl, imidazopyrimidinyl, indazolyl, indolyl, isobenzofuranyl, isoquinolyl, naphthyridyl, oxazolyl, phthalazinyl, pyranyl, pyrazinyl, pyridooxazinyl, pyridyl, pyrimidinyl, pyrrolizinyl, pyrrolopyridyl, thiazolyl, thienyl, triazolyl, pyrrolyl, pyrazolyl, triazinyl or triazolopyridinyl.

$C_{1-6}$alkyl may be straight-chain or branched and/or bridged and is for example methyl, ethyl, propyl, isopropyl, butyl, isobutyl, secondary butyl, tertiary butyl or a pentyl or hexyl group.

$C_{1-6}$Alkylamino is, for example, methylamino, ethylamino, propylamino or butylamino.

Di-$C_{1-6}$alkylamino is, for example, dimethylamino, N-methyl-N-ethylamino, diethylamino, N-methyl-N-propylamino or N-butyl-N-methylamino.

$C_{2-6}$alkenyl may be straight-chain or branched and is, for example, allyl or vinyl.

$C_{2-6}$alkynyl may be straight-chain or branched and is, for example, ethynyl.

$C_{1-6}$alkoxy is, for example, methoxy, ethoxy, propyloxy, isopropyloxy, butyloxy, isobutyloxy, secondary butyloxy, tertiary butyloxy, pentyloxy or hexyloxy.

$C_{1-6}$Alkoxycarbonylamino is preferably $C_2$-$C_5$alkoxycarbonylamino such as ethoxycarbonylamino, propyloxycarbonylamino, isopropyloxycarbonylamino, butyloxycarbonylamino, isobutyloxycarbonylamino, secondary butyloxycarbonylamino or tertiary butyloxycarbonylamino.

$C_{1-6}$alkylcarbonyloxy is, for example, acetyloxy, propionyloxy, propylcarbonyloxy, isopropylcarbonyloxy, butylcarbonyloxy, isobutylcarbonyloxy, secondary butylcarbonyloxy, tertiary butylcarbonyloxy, pentylcarbonyloxy or hexylcarbonyloxy.

$C_{0-6}$alkylcarbonylamino is, for example, formylamino, acetylamino, propionylamino, propylcarbonylamino, isopropylcarbonylamino, butylcarbonylamino, isobutylcarbonylamino, secondary butylcarbonylamino, tertiary butylcarbonylamino, pentylcarbonylamino or hexylcarbonylamino.

Halogen is, for example, fluorine, chlorine, bromine or iodine, preferably fluorine or chlorine.

Halo-$C_{1-6}$alkoxy is, for example, alkoxy substituted one or more times by fluorine, chlorine, bromine or iodine, including mixed, e.g. fluorine and chlorine, substitutions, with preference for perfluorinated radicals such as trifluoromethoxy.

Halo-$C_{1-4}$alkyl is, for example, alkyl substituted one or more times by fluorine, chlorine, bromine or iodine, including mixed, e.g. fluorine and chlorine, substitutions, with preference for perfluorinated radicals such as trifluoromethyl.

$C_{1-6}$Alkylenedioxy is, for example, methylenedioxy, ethylenedioxy, 1,3-propylenedioxy or 1,2-propylenedioxy.

Optionally N-mono- or N,N-di-$C_{1-8}$-alkylated carbamoyl is, for example, carbamoyl, methylcarbamoyl, ethylcarbamoyl, N,N-dimethylcarbamoyl, N,N-diethylcarbamoyl or propylcarbamoyl.

Optionally esterified carboxy is, for example, carboxy esterified with $C_{0-6}$alkyl, such as carboxy or $C_{1-6}$alkoxycarbonyl.

$C_{3-8}$Cycloalkoxy is preferably 3-, 5- or 6-membered cycloalkoxy such as cyclopropyloxy, cyclopentyloxy and cyclohexyloxy.

$C_{3-8}$Cycloalkyl-$C_{0-6}$alkyl is preferably 3-, 5- or 6-membered cycloalkyl such as cyclopropyl, cyclopropylmethyl, cyclopentyl and cyclohexyl.

Cyano-$C_{1-4}$alkoxy is, for example, cyanomethoxy, 2-cyanoethoxy, 2- or 3-cyanopropyloxy or 4-cyanobutyloxy, especially cyanomethoxy.

Cyano-$C_{1-4}$alkyl is, for example, cyanomethyl, 2-cyanoethyl, 2- or 3-cyanopropyl, 2-cyano-2-methylpropyl or 4-cyanobutyl, especially cyanomethyl.

N,N-Di-$C_{1-4}$alkylamino is, for example, dimethylamino, N-methyl-N-ethylamino, diethylamino, N-methyl-N-propylamino or N-butyl-N-methylamino.

N,N-Di-$C_{1-4}$alkylamino-$C_{1-4}$alkoxy is 2-dimethylaminoethoxy, 3-dimethylaminopropyloxy, 4-dimethylaminobutyloxy, 2-diethylaminoethoxy, 2-(N-methyl-N-ethylamino)ethoxy or 2-(N-butyl-N-methylamino)ethoxy.

N,N-Di-$C_{1-4}$alkylamino-$C_{1-4}$alkyl is, for example, 2-dimethylaminoethyl, 3-dimethylaminopropyl, 4-dimethylaminobutyl, 2-diethylaminoethyl, 2-(N-methyl-N-ethylamino)ethyl or 2-(N-butyl-N-methylamino)ethyl.

N,N-Di-$C_{1-4}$alkylcarbamoyl-$C_{1-4}$alkoxy is, for example, methyl- or dimethylcarbamoyl-$C_{1-4}$alkoxy such as N-methyl-, N-butyl- or N,N-dimethylcarbamoylmethoxy, 2-(N-methylcarbamoyl)ethoxy, 2-(N-butylcarbamoyl)ethoxy, 2-(N,N-dimethylcarbamoyl)ethoxy, 3-(N-methylcarbamoyl)propyloxy, 3-(N-butylcarbamoyl)propyloxy, 3-(N,N-dimethylcarbamoyl)propyloxy or 4-(N-methylcarbamoyl)butyloxy, 4-(N-butylcarbamoyl)butyloxy or 4-(N,N-dimethylcarbamoyl)butyloxy, especially N-methyl-, N-butyl- or N,N-dimethylcarbamoylmethoxy.

N,N-Di-$C_{1-4}$alkylcarbamoyl-$C_{1-4}$alkyl is, for example, 2-dimethylcarbamoylethyl, 3-dimethylcarbamoylpropyl, 2-dimethylcarbamoylpropyl, 2-(dimethylcarbamoyl)-2-methylpropyl or 2-(dimethylcarbamoyl)butyl.

Optionally partially hydrogenated pyridyl- or N-oxidopyridyl-$C_{1-4}$alkoxy is, for example, pyridyl- or N-oxidopyridylmethoxy, 2-pyridylethoxy, 2- or 3-pyridylpropyloxy or 4-pyridylbutyloxy, especially 3- or 4-pyridylmethoxy.

Optionally partially hydrogenated pyridyl- or N-oxidopyridyl-$C_{1-4}$alkyl is, for example, pyridyl- or N-oxidopyridylmethyl, 2-pyridylethyl, 2- or 3-pyridylpropyl or 4-pyridylbutyl, especially 3- or 4-pyridylmethyl.

Morpholino-$C_{1-4}$alkoxy may be N-oxidized and is, for example, 1-morpholinoethoxy, 3-morpholinopropyloxy or 1-(morpholino-2-methyl)propyloxy.

Morpholino-$C_{1-4}$alkyl may be N-oxidized and is, for example, morpholinomethyl, 2-morpholinoethyl, 3-morpholinopropyl or 1- or 2-(4-morpholino)butyl.

Piperazino-$C_{1-4}$alkyl is, for example, piperazinomethyl, 2-piperazinoethyl or 3-piperazinopropyl.

Piperidino-$C_{1-4}$alkoxy is, for example, piperidinomethoxy, 2-piperidinoethoxy or 3-piperidinopropyloxy.

Piperidino-$C_{1-4}$alkyl is, for example, piperidinomethyl, 2-piperidinoethyl or 3-piperidinopropyl.

Pyrrolidino-$C_{1-4}$alkoxy is, for example, 2-pyrrolidinoethoxy or 3-pyrrolidinopropyloxy.

Pyrrolidino-$C_{1-4}$alkyl is, for example, pyrrolidinomethyl, 2-pyrrolidinoethyl or 3-pyrrolidinopropyl.

S-Oxothiomorpholino-$C_{1-4}$alkyl is, for example, S-oxothiomorpholinomethyl or 2-(S-oxothiomorpholino)ethyl.

Thiazolyl-$C_{1-4}$alkoxy is, for example, thiazolylmethoxy, 2-thiazolylethoxy or 3-thiazolylpropyloxy.

Thiomorpholino-$C_{1-4}$alkyl or S,S-dioxothiomorpholino-$C_{1-4}$alkyl is, for example, thiomorpholino-$C_{1-4}$alkyl such as -methyl or -ethyl, or S,S-dioxothiomorpholino-$C_{1-4}$alkyl such as -methyl or -ethyl.

Depending on the presence of asymmetric carbon atoms, the compounds of the invention may be in the form of mixtures of isomers, specifically as racemates, or in the form of pure isomers, specifically of optical antipodes. The invention includes all these forms. Mixtures of diastereomers, diastereomeric racemates or mixtures of diastereomeric racemates can be fractionated by conventional methods, e.g. by column chromatography, thin-layer chromatography, HPLC and the like.

Salts of compounds with salt-forming groups are in particular acid addition salts, salts with bases or, if a plurality of salt-forming groups is present, optionally also mixed salts or inner salts.

Salts are primarily the pharmaceutically acceptable or non-toxic salts of compounds of the formula (I). Such salts are formed for example by compounds of the formula (I) having an acidic group, e.g. a carboxy or sulpho group, and are for example their salts with suitable bases, such as non-toxic metal salts derived from metals of group Ia, Ib, IIa and IIb of the Periodic Table of the Elements, e.g. alkali metal, in particular lithium, sodium or potassium, salts, alkaline earth metal salts, for example magnesium or calcium salts, furthermore zinc salts or ammonium salts, also those salts formed with organic amines such as optionally hydroxy-substituted mono-, di- or trialkylamines, especially mono-, di- or tri-lower-alkylamines, or with quaternary ammonium bases, e.g. methyl-, ethyl-, diethyl- or triethylamine, mono-, bis- or tris(2-hydroxy-lower-alkyl)amines such as ethanol-, diethanol- or triethanolamine, tris(hydroxymethyl)methylamine or 2-hydroxy-tertiary-butylamine, N,N-di-lower-alkyl-N-(hydroxy-lower-alkyl)amine, such as N,N-dimethyl-N-(2-hydroxyethyl)amine, or N-methyl-D-glucamine, or quaternary ammonium hydroxides such as tetrabutylammonium hydroxide. Under lower-alkyl is understood an alkyl group having 1 to 6 C-atoms. The compounds of the formula I having a basic group, e.g. an amino group, can form acid addition salts, e.g. with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, furthermore amino acids such as, for example, the α-amino acids mentioned hereinbelow, and methanesulphonic acid, ethanesulphonic acid, 2-hydroxyethanesulphonic acid, ethane-1,2-disulphonic acid, benzenesulphonic acid, 4-toluenesulphonic acid, naphthalene-2-sulphonic acid, 2- or 3-phosphoglycerate, glucose 6-phosphate, N-cyclohexylsulphamic acid (to form cyclamates) or with other acidic organic compounds such as ascorbic acid. Compounds of the formula (I) having acidic and basic groups may also form inner salts.

Pharmaceutically unsuitable salts may also be used for isolation and purification.

The compounds of the formula (I) also include compounds in which one or more atoms are replaced by their stable, non-radioactive isotopes; for example a hydrogen atom by deuterium.

Prodrug derivatives of the compounds described herein are derivatives thereof which on in vivo use liberate the original compound by a chemical or physiological process. A prodrug may for example be converted into the original compound when a physiological pH is reached or by enzymatic conversion. Possible examples of prodrug derivatives are esters of freely available carboxylic acids, S- and O-acyl derivatives of thiols, alcohols or phenols, the acyl group being defined as herein. Preferred derivatives are pharmaceutically acceptable ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters such as lower (amino, mono- or dialkylamino, carboxy, lower alkoxycarbonyl)-alkyl esters or such as lower α-(alkanoyloxy, alkoxycarbonyl or dialkylaminocarbonyl)-alkyl esters; conventionally, pivaloyloxymethyl esters and similar esters are used as such.

Because of the close relationship between a free compound, a prodrug derivative and a salt compound, a particular compound in this invention also includes its prodrug derivative and salt form, where this is possible and appropriate.

The groups of compounds mentioned hereinafter are not to be regarded as closed; on the contrary, it is possible for parts of these groups of compounds to be interchanged or replaced by the definitions given above, or omitted, in a worthwhile manner, e.g. to replace general by more specific definitions.

Preferred saturated oxygen-heterocyclyl radicals for $R^1$ are 4-16-membered, mono- or bicyclic saturated oxygen-heterocyclic radicals having 1 or 2 oxygen atoms. Preference is given to 4-8-membered, and particular preference to 5- or 6-membered, monocyclic radicals which optionally have a fused-on 3-8-membered ring which may be carbocyclic or heterocyclic. A further preferred group of oxygen-heterocyclic radicals for $R^1$ are bicyclic saturated oxygen-heterocycles which have for example a spirocyclic or bridged ring. Preferred heterocyclic radicals for $R^1$ have in each ring 1 oxygen atom or 1-2 oxygen atoms, with at least one, preferably 2-7, carbon atoms being present per ring.

$R^1$ is particularly preferably optionally substituted tetrahydrofuranyl, optionally substituted tetrahydrofuranylmethyl, optionally substituted tetrahydropyranyl or optionally substituted tetrahydropyranylmethyl.

$R^6$ is preferably a group —$CH_2$—$R^7$, —$CH_2$—CO—$R^7$ or —$CH_2$—$NR^8$—CO—$R^7$.

$R^7$ is preferably an optionally substituted aromatic or partially saturated heterocyclic radical.

$R^7$ is particularly preferably an optionally substituted phenyl, 2,3-dihydro-benzo[1,4]oxazinyl, 2,3-dihydro-benzo[1,4]thiazinyl or 1,2,3,4-tetrahydroquinolyl.

Examples of preferred substituents on $R^7$ in the meaning of phenyl are $C_{1-6}$-alkyl, halogen, trifluoromethyl, $C_{1-4}$-alkoxy-$C_{1-4}$-alkyl, $C_{1-4}$-alkoxy-$C_{1-4}$-alkoxy-$C_{1-4}$-alkyl, $C_{1-6}$-alkoxy and $C_{1-4}$-alkoxy-$C_{1-6}$-alkoxy.

Examples of preferred substituents on $R^7$ in the meaning of partially saturated heterocyclic are $C_{1-4}$-alkoxycarbonylamino such as methoxycarbonylamino, ethoxycarbonylamino, propoxycarbonylamino, isopropoxycarbonylamino or butoxycarbonylamino, $C_{1-4}$-alkoxy-$C_{1-4}$-alkoxy-$C_{1-4}$-alkyl, such as methoxy-$C_{1-4}$-alkoxy-$C_{1-4}$-alkyl, ethoxy-$C_{1-4}$-alkoxy-$C_{1-4}$-alkyl, propoxy-$C_{1-4}$-alkoxy-$C_{1-4}$-alkyl, isopropoxy-$C_{1-4}$-alkoxy-$C_{1-4}$-alkyl or butoxy-$C_{1-4}$-alkoxy-$C_{1-4}$-alkyl, where $C_{1-4}$-alkoxy is, for example, methoxy, ethoxy, propoxy or butoxy, and $C_{1-4}$-alkyl is, for example, methyl, ethyl, propyl or butyl, in particular methoxymethoxymethyl, 2-methoxyethoxymethyl or 3-methoxypropoxymethyl, $C_{1-4}$-alkoxy-$C_{1-4}$-alkyl, such as methoxy-$C_{1-4}$-alkyl, ethoxy-$C_{1-4}$-alkyl, propoxy-$C_{1-4}$-alkyl, isopropoxy-$C_{1-4}$-alkyl, butoxy-$C_{1-4}$-alkyl, isobutoxy-$C_{1-4}$-alkyl, sec-butoxy-$C_{1-4}$-alkyl or tert-butoxy-$C_{1-4}$-alkyl, where $C_{1-4}$-alkyl is, for example, methyl, ethyl, propyl or butyl, in particular ethoxymethyl or 2-methoxyethyl, or N—$C_{1-4}$-alkylcarbamoyl, such as N-methylcarbamoyl, N-ethylcarbamoyl, N-propylcarbamoyl or N-butylcarbamoyl.

$R^6$ is particularly preferably a group —$CH_2$—$R^7$ with $R^7$ being phenyl.

Preference is further given to compounds of the general formula

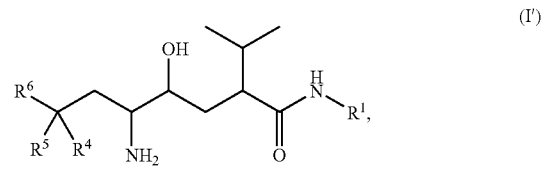

(I')

in which $R^1$, $R^4$, $R^5$ and $R^6$ have the meaning as indicated for the compound of the formula (I).

Particular preference is given in each case to those compounds of the formula (I') in which at least one, for example one, two, three or preferably all asymmetric carbon atoms of the main chain have the absolute stereochemistry shown in formula (I'A) ("S" in each case), where the substituents each have the meanings indicated above and their pharmaceutically acceptable salts.

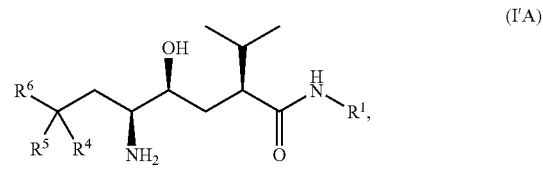

(I'A)

The above-mentioned preferences for the individual substituents or groups of substituents apply in the same way also to the compounds of the formulae (I') and (I'A).

The compounds of the formula (I), (I') and formula (I'A) can be prepared in an analogous manner to the preparation process disclosed in the literature (see WO 2002008172 and WO 2002/002508 and literature cited therein). Further preparation processes are described for example in EP 678503, EP 702004, WO 01/09079, WO 01/09083, WO 02/02487, EP 716007, WO 02/02500, WO 02/092828 and in Helvetica Chemica Acta 86 (2003), 2848-2870 and literature cited therein.

Details of the specific preparation variants can be found in the examples.

The compounds of the formula (I) can also be prepared in optically pure form. Separation into antipodes can take place by methods known per se, either preferably at an early stage in the synthesis by salt formation with an optically active acid such as, for example, (+) or (−)-mandelic acid and separation of the diastereomeric salts by fractional crystallization or preferably at a rather late stage by derivatizing with a chiral auxiliary component such as, for example, (+) or (−)-camphanoyl chloride, and separation of the diastereomeric products by chromatography and/or crystallization and subsequent cleavage of the linkage to the chiral auxiliary. The pure diastereomeric salts and derivatives can be analysed to determine the absolute configuration of the contained piperidine by conventional spectroscopic methods, with X-ray spectroscopy on single crystals representing a particularly suitable method.

The compounds of the formula (I), and of the formula (I'A), and their pharmaceutically acceptable salts have an inhibitory effect on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II raises the blood pressure both directly by arterial constriction, and indirectly by releasing the hormone aldosterone, which retains sodium ions, from the adrenals, which is associated with an increase in the extracellular fluid volume. This increase is attributable to the effect of angiotensin II itself or of the heptapeptide angiotensin III formed therefrom as cleavage product. Inhibitors of the enzymatic activity of renin bring about a reduction in the formation of angiotensin I and, as a consequence thereof, the formation of a smaller amount of angiotensin II. The reduced concentration of this active peptide hormone is the direct cause of the blood pressure-lowering effect of renin inhibitors.

The effect of renin inhibitors is detected inter alia experimentally by means of in vitro tests where the reduction in the formation of angiotensin I is measured in various systems (human plasma, purified human renin together with synthetic or natural renin substrate). The following in vitro test of Nussberger et al. (1987) J. Cardiovascular Pharmacol., Vol. 9, pp. 39-44, is used inter alia. This test measures the formation of angiotensin I in human plasma. The amount of angiotensin I formed is determined in a subsequent radio-immunoassay. The effect of inhibitors on the formation of angiotensin I is tested in this system by adding various concentrations of these substances. The $IC_{50}$ is defined as the concentration of the particular inhibitor which reduces the formation of angiotensin I by 50%.

The compounds of the present invention show inhibitory effects in the in vitro systems at minimal concentrations of about $10^6$ to about $10^{-10}$ mol/l.

The compound having Example number 1 shows an $IC_{50}$ of $2.6 \cdot 10^{-9}$ mol/l.

Renin inhibitors bring about a fall in blood pressure in salt-depleted animals. Human renin differs from renin of other species. Inhibitors of human renin are tested using primates (marmosets, *Callithrix jacchus*) because human renin and primate renin are substantially homologous in the enzymatically active region. The following in vivo test is employed inter alia: the test compounds are tested on normotensive marmosets of both sexes with a body weight of about 350 g, which are conscious, unrestrained and in their normal cages. Blood pressure and heart rate are measured with a catheter in the descending aorta and are recorded radiometrically. Endogenous release of renin is stimulated by combining a low-salt diet for 1 week with a single intramuscular injection of furosemide (5-(aminosulphonyl)-4-chloro-2-[(2-furanylmethyl)amino]benzoic acid) (5 mg/kg). 16 hours after the furosemide injection, the test substances are administered either directly into the femoral artery by means of a hypodermic needle or as suspension or solution by gavage into the stomach, and their effect on blood pressure and heart rate is evaluated. The compounds of the present invention have a blood pressure-lowering effect in the described in vivo test with i.v. doses of about 0.003 to about 0.3 mg/kg and with oral doses of about 0.3 to about 30 mg/kg.

The blood pressure-reducing effect of the compounds described herein can be tested in vivo using the following protocol:

The investigations take place in 5 to 6-week old, male double transgenic rats (dTGR), which overexpress both human angiotensinogen and human renin and consequently develop hypertension (Bohlender J. et al., J Am Soc Nephrol 2000; 11: 2056-2061). This double transgenic rat strain was produced by crossbreeding two transgenic strains, one for human angiotensinogen with the endogenous promoter and one for human renin with the endogenous promoter. Neither single transgenic strain was hypertensive. The double transgenic rats, both males and females, develop severe hypertension (mean systolic pressure, approximately 200 mm Hg) and die after a median of 55 days if untreated. The fact that human renin can be studied in the rat is a unique feature of this model. Age-matched Sprague-Dawley rats serve as non-hypertensive control animals. The animals are divided into treatment groups and receive test substance or vehicle (control) for various treatment durations. The applied doses for oral administration may range from 0.5 to 100 mg/kg body weight. Throughout the study, the animals receive standard feed and tap water ad libitum. The systolic and diastolic blood pressure, and the heart rate are measured telemetrically by means of transducers implanted in the abdominal aorta, allowing the animals free and unrestricted movement.

The effect of the compounds described herein on kidney damage (proteinuria) can be tested in vivo using the following protocol:

The investigations take place in 4-week old, male double transgenic rats (dTGR), as described above. The animals are divided into treatment groups and receive test substance or vehicle (control) each day for 7 weeks. The applied doses for oral administration may range from 0.5 to 100 mg/kg body weight. Throughout the study, the animals receive standard feed and tap water ad libitum. The animals are placed periodically in metabolism cages in order to determine the 24-hour urinary excretion of albumin, diuresis, natriuresis, and urine osmolality. At the end of the study, the animals are sacrificed and the kidneys and hearts may also be removed for determining the weight and for immunohistological investigations (fibrosis, macrophage/T cell infiltration, etc.).

The pharmacokinetic properties of the compounds described herein can be tested in vivo using the following protocol:

The investigations take place in pre-catheterized (carotid artery) male rats (300 g±20%) that can move freely throughout the study. The compound is administered intravenously and orally (gavage) in separate sets of animals. The applied doses for oral administration may range from 0.5 to 50 mg/kg body weight; the doses for intravenous administration may range from 0.5 to 20 mg/kg body weight. Blood samples are collected through the catheter before compound administration and over the subsequent 24-hour period using an automated sampling device (AccuSampler, DiLab Europe, Lund, Sweden). Plasma levels of the compound are determined using a validated LC-MS analytical method. The pharmacokinetic analysis is performed on the plasma concentration-time curves after averaging all plasma concentrations across time points for each route of administration. Typical pharmacokinetics parameters to be calculated include: maximum concentration ($C_{max}$), time to maximum concentration ($t_{max}$), area under the curve from 0 hours to the time point of the last quantifiable concentration ($AUC_{0-t}$), area under the curve from time 0 to infinity ($AUC_{0-inf}$), elimination rate constant (K), terminal half-life ($t_{1/2}$), absolute oral bioavailability or fraction absorbed (F), clearance (CL), and Volume of distribution during the terminal phase (Vd).

The compounds of the formula (I), and preferably of the formula (I'A), and their pharmaceutically acceptable salts can be used as medicines, e.g. in the form of pharmaceutical products. The pharmaceutical products can be administered enterally, such as orally, e.g. in the form of tablets, lacquered tablets, sugar-coated tablets, hard and soft gelatine capsules, solutions, emulsions or suspensions, nasally, e.g. in the form of nasal sprays, rectally, e.g. in the form of suppositories, or transdermally, e.g. in the form of ointments or patches. However, administration is also possible parenterally, such as intramuscularly or intravenously, e.g. in the form of solutions for injection.

Tablets, lacquered tablets, sugar-coated tablets and hard gelatine capsules can be produced by processing the compounds of the formula (I), or preferably of the formula (I'A), and their pharmaceutically acceptable salts with pharmaceutically inert inorganic or organic excipients. Excipients of these types which can be used for example for tablets, sugar-coated tablets and hard gelatine capsules are lactose, maize starch or derivatives thereof, talc, stearic acid or salts thereof etc.

Excipients suitable for soft gelatine capsules are, for example, vegetable oils, waxes, fats, semisolid and liquid polyols etc.

Excipients suitable for producing solutions and syrups are, for example, water, polyols, sucrose, invert sugar, glucose etc.

Excipients suitable for solutions for injection are, for example, water, alcohols, polyols, glycerol, vegetable oils, bile acids, lecithin etc.

Excipients suitable for suppositories are, for example, natural or hardened oils, waxes, fats, semiliquid or liquid polyols etc.

The pharmaceutical products may in addition comprise preservatives, solubilizers, viscosity-increasing substances, stabilizers, wetting agents, emulsifiers, sweeteners, colorants, aromatizers, salts to alter the osmotic pressure, buffers, coating agents or antioxidants. They may also comprise other substances of therapeutic value.

The present invention further provides the use of the compounds of the formula (I), or preferably of the formula (I'A), and their pharmaceutically acceptable salts in the treatment or prevention of high blood pressure, heart failure, glaucoma, myocardial infarction, renal failure and restenoses.

The compounds of the formula (I), and preferably of the formula (I'A), and their pharmaceutically acceptable salts can also be administered in combination with one or more agents having cardiovascular activity, e.g. α- and β-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as aminone, bencyclan, diltiazem, fendiline, flunarizine, nicardipine, nimodipine, perhexyline, verapamil, gallopamil, nifedipine etc.; ACE inhibitors such as cilazapril, captopril, enalapril, lisinopril etc.; potassium activators such as pinacidil; antiserotoninergics such as ketanserine; thromboxane synthetase inhibitors; neutral endopeptidase inhibitors (NEP inhibitors); angiotensin II antagonists; and diuretics such as hydrochlorothiazide, chlorothiazide, acetazolamide, amiloride, bumetanide, benzthiazide, ethacrynic acid, furosemide, indacrinone, metolazone, spironolactone, triamterene, chlorthalidone etc.; sympatholytics such as methyldopa, clonidine, guanabenz, reserpine; and other agents suitable for the treatment of high blood pressure, heart failure or vascular disorders associated with diabetes or renal disorders such as acute or chronic renal failure in humans and animals. Such combinations can be used separately or in products which comprise a plurality of components.

Further substances which can be used in combination with the compounds of the formulae (I) or (I'A) are the compounds of classes (i) to (ix) on page 1 of WO 02/40007 (and the preferences and examples detailed further therein) and the substances mentioned on pages 20 and 21 of WO 03/027091.

The dosage may vary within wide limits and must of course be adapted to the individual circumstances in each individual case. In general, a daily dose appropriate for oral administration ought to be from about 3 mg to about 3 g, preferably about 10 mg to about 1 g, e.g. approximately 300 mg per adult person (70 kg), divided into preferably 1-3 single doses, which may be for example of equal size, although the stated upper limit may also be exceeded if this proves to be indicated, and children usually receive a reduced dose appropriate for their age and body weight.

EXAMPLES

The following examples illustrate the present invention. All temperatures are stated in degrees Celsius and pressures in mbar. Unless mentioned otherwise, the reactions take place at room temperature. The abbreviation "Rf=xx (A)" means for example that the Rf is found in solvent system A to be xx. The ratio of amounts of solvents to one another is always stated in parts by volume. Chemical names for final products and intermediates have been generated on the basis of the chemical structural formulae with the aid of the AutoNom 2000 (Automatic Nomenclature) program. Unless mentioned otherwise, the absolute stereochemistry of all four asymmetric C atoms in the main chain is "S" in each case.

HPLC gradients on Hypersil BDS C-18 (5 um); column: 4×125 mm
I 90% water*/10% acetonitrile* to 0% water*/100% acetonitrile* in 5 minutes+2.5 minutes (1.5 ml/min)
II 95% water*/5% acetonitrile* to 0% water*/100% acetonitrile* in 40 minutes (0.8 ml/min)
* contains 0.1% trifluoroacetic acid
The following abbreviations are used:

| | |
|---|---|
| Rf | ratio of distance migrated by a substance to the distance of the solvent front from the starting point in thin-layer chromatography |
| Rt | retention time of a substance in HPLC (in minutes) |
| M.p. | melting point (temperature) |

General Method A: (Azide Reduction)
A solution of 1 mmol of "azide derivative" in 10-20 ml of ethanol and ethanolamine (1 equiv) is hydrogenated in the presence of 200-400 mg of Pd/C 10% (moist) at 0° C. for 1-3 hours. The reaction mixture is clarified by filtration and the catalyst is washed with ethanol. The filtrate is evaporated. The title compound is obtained from the residue by flash chromatography ($SiO_2$ 60 F).

General Method B: (Lactone Amidation I)

A mixture of 1 mmol of "lactone", "amine" (10-30 equiv.) and 2-hydroxypyridine (1 equiv.) is stirred at 65° C. for 2-24 hours. The reaction mixture is cooled to room temperature, evaporated, mixed with 1 M aqueous sodium bicarbonate solution and extracted with tert-butyl methyl ether (2×). The combined organic phases are washed with water and brine, dried with sodium sulphate and evaporated. The title compound is obtained from the residue by flash chromatography ($SiO_2$ 60 F).

General Method C: (Lactone Amidation II)

A solution of 1.2 mmol of "amine" in 1-2 ml of toluene is added to a solution of 1.1 mmol of trimethylaluminium solution (2 M in heptane) at −78° C. The reaction mixture is warmed to room temperature, stirred for a further 30-60 minutes and then evaporated. A solution of 1 mmol of "lactone" in 2 ml of toluene is added to the residue, and the mixture is stirred at 80° C. for 24 hours. The reaction mixture is cooled to room temperature and, after addition of 10 ml of 1N HCl, stirred for 30 minutes. The reaction mixture is diluted with brine and extracted with toluene (2×)—the combined organic phases are dried with sodium sulphate and evaporated. The title compound is obtained from the residue by flash chromatography ($SiO_2$ 60 F).

General Method D: (Desilylation)

1.5 mmol of tetrabutylammonium fluoride solution (1M in tetrahydrofuran) are added to a solution of 1 mmol of "silyl ether" in 10-15 ml of tetrahydrofuran at 0° C. The reaction mixture is stirred at room temperature for 24 hours, poured into 1M aqueous sodium bicarbonate solution and extracted with tert-butyl methyl ether (2×). The combined organic phases are washed with brine, dried with sodium sulphate and evaporated. The title compound is obtained from the residue by flash chromatography ($SiO_2$ 60 F).

General Method E: (Chloro Enamine Coupling)

1.2-1.8 mmol of (1-chloro-2-methylpropenyl)dimethylamine (chloro enamine) are added to a solution of 1 mmol of "acid" in 10 ml of dichloromethane at 0° C. After 24 hours, the reaction mixture is evaporated and the residue is dissolved in 6 ml of dichloromethane—this solution is added dropwise to the solution of 1.25 mmol of "amine" and 1.1 mmol of triethylamine in 6 ml of dichloromethane at 0° C. over the course of 2-10 minutes. The reaction mixture is stirred at room temperature for 1-2 hours, poured into water and extracted with tert-butyl methyl ether (2×). The combined organic phases are washed with brine, dried with sodium sulphate and evaporated. The title compound is obtained from the residue by flash chromatography ($SiO_2$ 60 F).

General Method F: (Lactone Opening/Silylation)

A solution of 1 mmol of "lactone" in 5 ml of dioxane is mixed with 5 ml of water and 1.1 mmol of lithium hydroxide monohydrate. After 4-6 hours, the reaction mixture is mixed with ice and 1M aqueous citric acid solution and extracted with tert-butyl methyl ether (3×). The combined organic phases are washed with cold water and cold brine, dried with sodium sulphate and evaporated at room temperature. The residue is dissolved without delay in 8 ml of N,N-di-methylformamide and then 5 mmol of tert-butylchlorodimethylsilane and 8.8 mmol of imidazole are added. After 10-20 hours, the reaction mixture is evaporated—the residue is mixed with diethyl ether and water and adjusted to pH 4 with 1M aqueous citric acid solution and then the organic phase is separated off. The aqueous phase is extracted again with diethyl ether (3×)—the combined organic phases are washed with brine, dried with sodium sulphate and evaporated. The residue is dissolved in 3 ml of tetrahydrofuran, and 3 ml of water and 9 ml of acetic acid are successively added. After 34 hours, the reaction mixture is poured into ice-water and extracted with diethyl ether (2×)—the combined organic phases are washed with water and brine, dried with sodium sulphate and evaporated. The title compound is obtained from the residue by flash chromatography ($SiO_2$ 60 F).

General Method G: (Grignard Reaction)

A solution of 1.33 mmol of "aryl bromide" in 2.70 ml of tetrahydrofuran is cooled to −78° C., and 2 mmol of N-methylmorpholine are added. Then 1.33 mmol of butyllithium solution (1.6 M in hexane) are added at −78° C. The reaction mixture is stirred at −78° C. for 5 minutes, and 2 mmol of magnesium bromide solution (0.3 M, freshly prepared from 2 mmol of Mg turnings and 2 mmol of 1,2-dibromoethane in 6.67 ml of tetrahydrofuran at 60° C.) are added. The reaction mixture is stirred at −78° C. and, after 5 minutes, a solution of 1 mmol of 2-[2-azido-2-(4-isopropyl-5-oxotetrahydrofuran-2-yl)ethyl]-3-methylbutyraldehyde [173154-024] in 1 ml of tetrahydrofuran is added at −78° C. The reaction mixture is then stirred at −78° C. for 15 minutes and quenched with 1M aqueous ammonium chloride solution. It is extracted with tert-butyl methyl ether (3×). The combined organic phases are washed with brine, dried with sodium sulphate and evaporated. The title compound is obtained from the residue by flash chromatography ($SiO_2$ 60 F).

General Method H: (Alcohol Methoxyacetylation)

2.6 mmol of pyridine, 2.4 mmol of methoxyacetyl chloride and 0.1 mmol of 4-dimethylaminopyridine are successively added to a solution of 1 mmol of "alcohol" in 13.5 ml of toluene at 0° C. The ice bath is removed and the reaction mixture is stirred at room temperature for 2 hours. The reaction mixture is poured into 0.5 M HCl and then the organic phase is separated off. The aqueous phase is extracted again with diethyl ether (3×)—the combined organic phases are washed with brine, dried with sodium sulphate and evaporated. The title compound is obtained from the residue by flash chromatography ($SiO_2$ 60 F).

General Method I: (Azide and Methoxyacetoxy Reduction)

A solution of 1 mmol of "azide methoxyacetoxy derivative" in 25 ml of ethanol and ethanolamine (1 mmol) is hydrogenated in the presence of 600 mg of Pd/C 10% (dry) at room temperature for 2-5 hours. The reaction mixture is clarified by filtration and the catalyst is washed with ethanol. The filtrate is evaporated. The residue is treated with 1 M sodium bicarbonate solution and extracted with tert-butyl methyl ether (3×)—the combined organic phases are dried with sodium sulphate and evaporated. The title compound is obtained from the residue by flash chromatography ($SiO_2$ 60 F).

General Method J: (Boc Protection of Amine)

2 mmol of N,N-diisopropylethylamine and 2 mmol of di-tert-butyl dicarbonate are successively added to a solution of 1 mmol of "amine" in 22 ml of dichloromethane at 0° C. The reaction mixture is warmed to room temperature and stirred at room temperature overnight. The reaction mixture is poured into water and then the organic phase is separated off. The aqueous phase is again extracted with dichloromethane (2×)—the combined organic phases are washed with brine, dried with sodium sulphate and evaporated. The title compound is obtained from the residue by flash chromatography ($SiO_2$ 60 F).

General Method K: (Boc Deprotection of Amine)

50 mmol of trifluoroacetic acid are added to a solution of 1 mmol of "amine" in 20 ml of dichloromethane at 0° C. The reaction mixture is stirred at 0° C. for 1-3 hours. The reaction mixture is neutralized with 1M sodium bicarbonate solution, and the aqueous phase is extracted with tert-butyl methyl ether (3×)—the combined organic phases are washed with, brine, dried with sodium sulphate and evaporated. The title compound is obtained from the residue by flash chromatography ($SiO_2$ 60 F).

General Method L: (Phenol Alkylation)

A solution of 1 mmol of "phenol" in 2 ml of dimethylformamide is mixed with 1.5 mmol of potassium carbonate and 1.1 mmol of 1-chloro-3-methoxypropane. The reaction mixture is stirred at 100° C. for 11 hours. The reaction mixture is filtered and evaporated. The residue is partitioned between ethyl acetate and water/brine 9:1. The phases are separated, the aqueous phase is extracted with ethyl acetate (2×)—the combined organic phases are washed with brine, dried with sodium sulphate and evaporated. The title compound is obtained from the residue by flash chromatography ($SiO_2$ 60 F).

Example 1

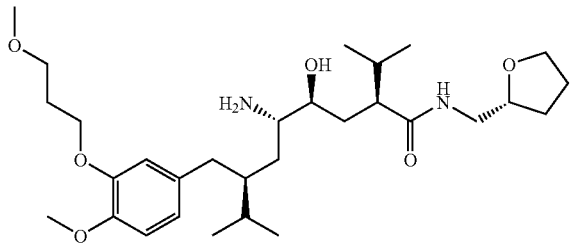

5-Amino-4-hydroxy-2-isopropyl-7-[4-methoxy-3-(3-methoxypropoxy)benzyl]-8-methyl-N-(tetrahydrofuran-2(R)-ylmethyl)nonamide The title compound is prepared as a yellowish oil in analogy to Method A from 0.36 g of 5-azido-4-hydroxy-2-isopropyl-7-[4-methoxy-3-(3-methoxypropoxy)benzyl]-8-methyl-N-(tetrahydrofuran-2(R)-ylmethyl)nonamide. Rf=0.40 (dichloromethane/methanol/conc. ammonia 25% 200:20:1). Rt=3.78 (gradient 1).

The starting materials are prepared as follows:

a) 5-Azido-4-hydroxy-2-isopropyl-7-[4-methoxy-3-(3-methoxypropoxy)benzyl]-8-methyl-N-(tetrahydrofuran-2(R)-ylmethyl)nonamide 0.46 g of 5-azido-4-(tert-butyldimethylsilanyloxy)-2-isopropyl-7-[4-methoxy-3-(3-methoxypropoxy)benzyl]-8-methyl-N-(tetrahydrofuran-2(R)-ylmethyl)nonamide is reacted in analogy to Method D. The title compound is obtained as a colourless oil. Rf=0.29 (EtOAc/heptane 3:1); Rt=4.85 (gradient I).

b) 5-Azido-4-(tert-butyldimethylsilanyloxy)-2-isopropyl-7-[4-methoxy-3-(3-methoxypropoxy)benzyl]-8-methyl-N-(tetrahydrofuran-2(R)-ylmethyl)nonamide 0.40 g of 5-Azido-4-(tert-butyldimethylsilanyloxy)-2-isopropyl-7-[4-methoxy-3-(3-methoxypropoxy)benzyl]-8-methylnonanoic acid and 0.10 ml of C-(tetrahydrofuran-2(R)-yl)methylamine are reacted in analogy to Method E. The crude title compound is obtained as a yellow oil.

c) 5-Azido-4-(tert-butyldimethylsilanyloxy)-2-isopropyl-7-[4-methoxy-3-(3-methoxypropoxy)benzyl]-8-methylnonanoic acid 0.933 g of 5-{1-azido-3-[4-methoxy-3-(3-methoxypropoxy)benzyl]-4-methylpentyl}-3-isopropyldihydrofuran-2-one [324763-46-4] is reacted in analogy to Method F. The title compound is obtained as a yellowish oil. Rf=0.40 (EtOAc/heptane 1:1); Rt=6.54 (gradient I).

The following compounds are prepared in an analogous manner to the process described in Example 1:

2 5-Amino-4-hydroxy-2-isopropyl-7-[4-methoxy-3-(3-methoxypropoxy)benzyl]-8-methyl-N-(tetrahydropyran-3(S)-ylmethyl)nonamide

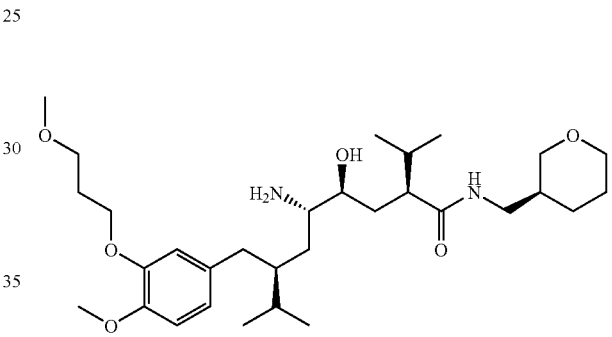

The starting material is prepared as follows:

a) C-(Tetrahydropyran-3S-yl)methylamine

A solution of 0.9 mmol of tetrahydropyran-3R-carbaldehyde [143810-10-0] in 5 ml of ethanol is mixed with a solution of 1.8 mmol of hydroxylamine hydrochloride in 0.5 ml of water and heated to reflux overnight. The reaction mixture is concentrated and partitioned between saturated sodium carbonate solution and diethyl ether. The phases are separated and the aqueous phase is extracted with diethyl ether (2×). The combined organic phases are dried with sodium sulphate and evaporated. The residue is dissolved in 5 ml of ethanol and, over the course of 2 hours, small portions of 12.8 mmol of zinc dust and of 0.8 ml of glacial acetic acid are added alternately. The internal temperature must not exceed 50° C. during the addition. The reaction mixture is stirred at room temperature for 12 hours and filtered through Hyflo, and the filter cake is washed with cold ethanol. The solution is evaporated and the residue is partitioned between 4M NaOH and diethyl ether. The phases are separated and the aqueous phase is extracted with diethyl ether (2×). The combined organic phases are dried with sodium sulphate and evaporated. The

3 5-Amino-4-hydroxy-2-isopropyl-7-[4-methoxy-3-(3-methoxypropoxy)benzyl]-8-methyl-N-(7-oxabicyclo[2.2.1]hept-2(R,S)-yl)nonamide

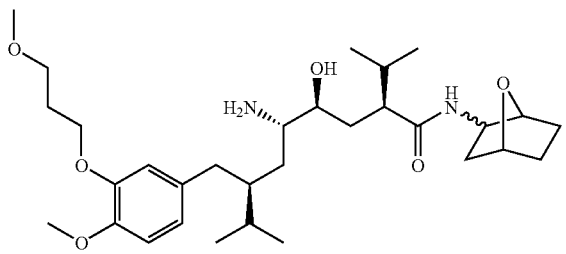

The starting material is prepared as follows:

a) 7-Oxabicyclo[2.2.1]hept-2(R,S)ylamine

A solution of 0.398 mmol of 7-oxabicyclo[2.2.1]heptane-2(R,S)carboxylic acid [19800-01-2] and 0.995 mmol of triethylamine in 4 ml of tetrahydrofuran is cooled to 0° C., and 0.796 mmol of ethyl chloroformate is added. The reaction mixture is stirred at 0° C. for 1 hour and then a solution of 7.96 mmol of sodium azide in 2 ml of water is added at 0° C. The reaction solution is stirred at 0° C. for 45 minutes. It is diluted with water and ethyl acetate, and the organic phase is washed with water (2×), dried with sodium sulphate and evaporated. The residue is taken up in 2 ml of toluene and heated at 115° C. for 2 hours. The reaction mixture is cooled to room temperature, mixed with 4N HCl and vigorously stirred at room temperature for 2 hours. The reaction mixture is evaporated. The crude title compound is identified from the residue on the basis of its Rf.

The starting material can alternatively be prepared as follows:

A solution of 29.4 mmol of 2(R,S)nitro-7-oxabicyclo[2.2.1]heptane [89210-62-8], [58564-86-6] in 60 ml of methanol and 147 mmol of ammonium formate is mixed with 235 mmol of Pd/C 10% and stirred at room temperature for 4 hours. It is filtered through Hyflo and the filtrate is evaporated. The residue is mixed with water and diethyl ether, the phases are separated, and the aqueous phase is extracted with diethyl ether (3×). The combined organic phases are washed with water and brine, dried with sodium sulphate and evaporated. The title compound is identified from the residue on the basis of its Rf by flash chromatography (SiO₂ 60 F).

4 5-Amino-4-hydroxy-2-isopropyl-7-[4-methoxy-3-(3-methoxypropoxy)benzyl]-8-methyl-N—((Z)-3-oxabicyclo[3.1.0]hex-1-ylmethyl)nonamide

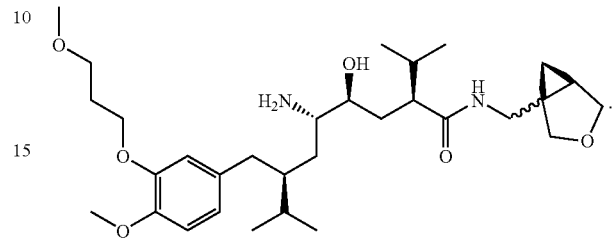

The starting materials are prepared as follows:

a) C—((Z)-3-Oxabicyclo[3.1.0]hex-1-yl)methylamine

A solution of 2.62 mmol of 1-azidomethyl-((Z)-3-oxabicyclo[3.1.0]hexane) in 150 ml of methanol is hydrogenated in the presence of 0.03 mmol of Pd/C 10% (moist) until conversion is complete. The reaction mixture is clarified by filtration and the catalyst is washed with ethanol. The filtrate is evaporated. The crude title compound is identified from the residue on the basis of its Rf.

b) 1-Azidomethyl-((Z)-3-oxabicyclo[3.1.0]hexane)

A solution of 5 mmol of (Z)-3-oxabicyclo[3.1.0]hex-1-ylmethyl methanesulphonate and 55 mmol of sodium azide in 50 ml of dimethyl sulphoxide is stirred at room temperature for 20 hours. It is then diluted with water and tert-butyl methyl ether and washed with brine. The aqueous phase is extracted with tert-butyl methyl ether (2×). The combined organic phases are dried with sodium sulphate and evaporated. The title compound is identified from the residue on the basis of its Rf.

c) (Z)-3-Oxabicyclo[3.1.0]hex-1-ylmethyl methanesulphonate 50 mmol of triethylamine and 20 mmol of methanesulphonyl chloride are successively added to a solution of 10 mmol of ((Z)-3-oxabicyclo[3.1.0]hex-1-yl)methanol in 100 ml of dichloromethane at 0° C. The mixture is stirred at 0° C. for 1 hour, diluted with dichloromethane and washed with M HCl. The organic phase is dried with sodium sulphate and evaporated. The crude title compound is identified from the residue on the basis of its Rf.

d) ((Z)-3-Oxabicyclo[3.1.0]hex-1-yl)methanol 0.42 mmol of tert-butyldimethyl-((Z)-3-oxabicyclo[3.1.0]hex-1-ylmethoxy)silane is reacted in analogy to Method D. The title compound is identified on the basis of its Rf.

e) tert-Butyldimethyl-((Z)-3-oxabicyclo[3.1.0]hex-1-ylmethoxy)silane 5.07 mmol of diethyl zinc and 10.02 mmol of chloroiodomethane are successively added dropwise to a solution of 2.52 mmol of tert-butyl(2,5-dihydrofuran-3-ylmethoxy) dimethylsilane [144186-63-0] in 12.5 ml of dichloroethane at 0° C. The reaction mixture is stirred at 0° C. for 20 minutes and then cautiously quenched with saturated ammonium chloride solution at 0° C. The mixture is warmed to room temperature and vigorously stirred for 10 minutes. It is extracted with tert-butyl methyl ether (3×), and the combined organic phases are washed with water and brine, dried with sodium sulphate and evaporated. The title compound is identified from the residue on the basis of its Rf by flash chromatography ($SiO_2$ 60 F).

The invention claimed is:

1. A compound of the formula

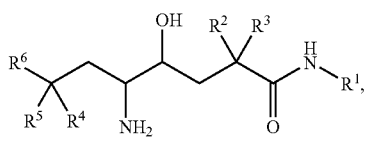

(I)

or a salt thereof; in which
$R^1$ is 7-oxabicyclo[2.2.1]heptanyl-;
$R^2$ and $R^3$ are independently of one another hydrogen, $C_{1-6}$alkyl, $C_{2-6}$alkenyl or $C_{2-6}$alkynyl, or the two radicals together with the carbon atom to which they are bonded are $C_{3-8}$cycloalkyl;
$R^4$ and $R^5$ are independently of one another hydrogen, $C_{1-6}$alkyl, $C_{2-6}$alkenyl or $C_{2-6}$alkynyl or the two radicals together with the carbon atom to which they are bonded are $C_{3-8}$cycloalkyl;
$R^6$ is a group —$CH_2$—$R^7$, —$CH_2$—CO—$R^7$, —$CH_2$—$CH_2$—$R^7$, —$CH_2$—$NR^8$—CO—$R^7$, —$CH_2$—CO—$NR^8$—$R^7$, —$CH_2$—$CH_2$—$NR^8$—$R^7$, —$CH_2$—CO—$NR^8$—$R^7$ or —CO—$NR^8$—$CH_2$—$R^7$;
$R^7$ is optionally substituted phenyl, 2,3-dihydro-benzo[1,4]oxazinyl, 2,3-dihydro-benzo[1,4]thiazinyl or 1,2,3,4-tetrahydroquinolyl, wherein when $R^7$ is phenyl the optional substituents are selected from the group consisting of $C_{1-6}$-alkyl, halogen, trifluoromethyl, $C_{1-4}$-alkoxy-$C_{1-4}$-alkyl, $C_{1-4}$-alkoxy-$C_{1-4}$-alkoxy-$C_{1-4}$-alkyl, $C_{1-6}$-alkoxy and $C_{1-4}$-alkoxy-$C_{1-6}$-alkoxy, and when $R^7$ is 2,3-dihydro-benzo[1,4]oxazinyl, 2,3-dihydro-benzo[1,4]thiazinyl or 1,2,3,4-tetrahydroquinolyl the optional substituents are selected from the group consisting of $C_{1-4}$-alkoxycarbonylamino, $C_{1-4}$-alkoxy-$C_{1-4}$-alkyl, $C_{1-4}$-alkoxy-$C_{1-4}$-alkyl, and N—$C_{1-4}$-alkylcarbamoyl; and
$R^8$ is hydrogen, $C_{1-6}$alkyl or $C_{1-6}$alkanoyl.

2. A pharmaceutically useful salt of a compound according to claim 1.

3. A compound according to claim 1 of formula (I')

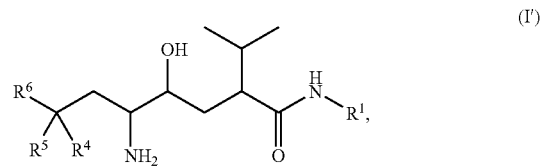

or a salt thereof; in which
$R^1$, $R^4$, $R^5$ and $R^6$ have the meaning as indicated for the compound of the formula (I) according to claim 1.

4. A pharmaceutically useful salt of a compound according to claim 3.

5. A pharmaceutical composition, comprising a compound of the formula (I) or a pharmaceutically useful salt thereof, according to claim 1, and a pharmaceutically inert excipient.

6. A pharmaceutical combination in the form of a product or of a kit comprising individual components a) of a compound of the formula (I) or a pharmaceutically useful salt thereof, according to claim 1, and b) of at least one pharmaceutical form whose active ingredient has a cardiovascular effect.

7. A compound according to claim 1, in which the optional substituents for 2,3-dihydro-benzo[1,4]oxazinyl, 2,3-dihydro-benzo[1,4]thiazinyl and 1,2,3,4-tetrahydroquinolyl are selected from the group consisting of methoxycarbonylamino, ethoxycarbonylamino, propoxycarbonylamino, isopropoxycarbonylamino, butoxycarbonylamino, methoxy-$C_{1-4}$-alkoxy-$C_{1-4}$-alkyl, ethoxy-$C_{1-4}$-alkoxy-$C_{1-4}$-alkyl, propoxy-$C_{1-4}$-alkoxy-$C_{1-4}$-alkyl, isopropoxy-$C_{1-4}$-alkoxy-$C_{1-4}$-alkyl, butoxy-$C_{1-4}$-alkoxy-$C_{1-4}$-alkyl, methoxy-$C_{1-4}$-alkyl, ethoxy-$C_{1-4}$-alkyl, propoxy-$C_{1-4}$-alkyl, isopropoxy-$C_{1-4}$-alkyl, butoxy-$C_{1-4}$-alkyl, isobutoxy-$C_{1-4}$-alkyl, sec-butoxy-$C_{1-4}$-alkyl, tert-butoxy-$C_{1-4}$-alkyl, N-methylcarbamoyl, N-ethylcarbamoyl, N-propylcarbamoyl and N-butylcarbamoyl.

8. A compound according to claim 7, in which the $C_{1-4}$-alkoxy is methoxy, ethoxy, propoxy or butoxy, and the $C_{1-4}$-alkyl is methyl, ethyl, propyl or butyl.

9. A compound according to claim 1, in which the $C_{1-4}$-alkoxy-$C_{1-4}$-alkoxy-$C_{1-4}$-alkyl is methoxymethoxymethyl, 2-methoxyethoxymethyl or 3-methoxypropoxymethyl, and the $C_{1-4}$-alkoxy-$C_{1-4}$-alkyl is ethoxymethyl or 2-methoxyethyl.

10. A compound according to claim 1 having the formula:

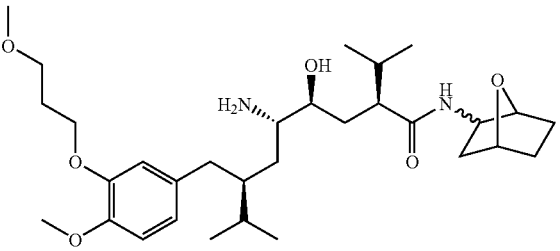

or a pharmaceutically acceptable salt thereof.

* * * * *